United States Patent
Goetzl

(10) Patent No.: US 10,203,342 B2
(45) Date of Patent: Feb. 12, 2019

(54) BIOMARKERS AND DIFFERENTIAL DIAGNOSIS OF ALZHEIMER'S DISEASE AND OTHER NEURODEGENERATIVE DISORDERS

(71) Applicant: NANOSOMIX, INC., Aliso Viejo, CA (US)

(72) Inventor: Edward J. Goetzl, San Francisco, CA (US)

(73) Assignee: NANOSOMIX, INC., Aliso Viejo, CA (US)

( * ) Notice: Subject to any disclaimer, the term of this patent is extended or adjusted under 35 U.S.C. 154(b) by 0 days.

(21) Appl. No.: 15/179,761

(22) Filed: Jun. 10, 2016

(65) Prior Publication Data

US 2016/0363599 A1 Dec. 15, 2016

Related U.S. Application Data

(60) Provisional application No. 62/174,436, filed on Jun. 11, 2015.

(51) Int. Cl.
*G01N 33/68* (2006.01)

(52) U.S. Cl.
CPC . *G01N 33/6896* (2013.01); *G01N 2333/4704* (2013.01); *G01N 2800/2814* (2013.01); *G01N 2800/2821* (2013.01); *G01N 2800/52* (2013.01)

(58) Field of Classification Search
None
See application file for complete search history.

(56) References Cited

PUBLICATIONS

Lu et al. Rest and stress resistance in ageing and Alzheimer's disease. Nature, 507:448-454, 2014.*
Liu et al. Deficiency in LRP6-mediated Wnt signaling contributes to synaptic abnormalities and amyloid pathology in Alzheimer's disease. Neuron, 84:63-77, 2014.*
Rajendran et al. Alzheimer's disease beta-amyloid peptides are released in association with exosomes. PNAS, 103:11172-11177, 2006.*
Goetzl et al., Low neural exosomal levels of cellular survival factors in Alzheimer's disease, Annals of Clinical and Translational Neurology, 2(7): 769-773, May 13, 2015.*

* cited by examiner

*Primary Examiner* — Kimberly Ballard
*Assistant Examiner* — Stacey N Macfarlane
(74) *Attorney, Agent, or Firm* — Law Office of Christopher Jacob, P.C.

(57) ABSTRACT

The present invention relates to biomarkers and diagnostic and prognostic methods for Alzheimer's disease and other neurodegenerative disorders. The invention also provides compositions for detecting the biomarker as well as compositions and methods useful for treating Alzheimer's disease and other neurodegenerative disorders.

1 Claim, 8 Drawing Sheets

US 10,203,342 B2

BIOMARKERS AND DIFFERENTIAL DIAGNOSIS OF ALZHEIMER'S DISEASE AND OTHER NEURODEGENERATIVE DISORDERS

RELATED APPLICATIONS

This application claims priority to the U.S. Provisional Patent Application Ser. No. 62/174,436, filed on Jun. 11, 2015, which is hereby incorporated by reference herein in its entirety.

FIELD OF THE INVENTION

The present invention relates to biomarkers and diagnostic and prognostic methods for Alzheimer's disease and other neurodegenerative disorders. The invention also provides compositions for detecting the biomarker as well as compositions and methods useful for treating Alzheimer's disease and other neurodegenerative disorders.

BACKGROUND OF THE INVENTION

More than 5.4 million Americans and 35 million people worldwide have Alzheimer's disease, the most common form of dementia. Currently, the only definitive way to diagnose Alzheimer's disease is by direct examination of brain tissue after a patient dies. Doctors use brain imaging, evaluation of behavior, psychiatric tests, and other means to diagnose the disease in the patients suspected of having Alzheimer's disease, but none are highly accurate, and many are costly or not practical.

Therefore, there is a need in the art for biomarkers and methods for diagnosing Alzheimer's disease and other neurodegenerative disorders. Additionally, there is a need in the art for compositions for detecting the biomarkers as well as compositions and methods useful for treating Alzheimer's disease and other neurodegenerative disorders. The present invention meets this need by providing accurate, noninvasive methods for diagnosing Alzheimer's disease and other neurodegenerative disorders. The present invention further provides novel methods, assays, kits, and compositions for diagnosing, prognosing, predicting, and treating Alzheimer's disease and other neurodegenerative disorders.

SUMMARY OF THE INVENTION

The present invention provides methods of analyzing a sample from a subject comprising the steps of: (i) obtaining a biological sample comprising vesicles from the subject, (ii) processing the sample to isolate or enrich the sample for the vesicles, and (iii) detecting the level of one or more biomarkers in the biological sample, wherein at least one of the one or more biomarkers is selected from the group consisting of low-density lipoprotein receptor-related protein 6 (LPR6), heat-shock factor-1 (HSF1), and repressor element 1-silencing transcription factor (REST). In other embodiments, the present invention provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: assaying the level of one or more biomarkers in a biological sample from the subject; and diagnosing or prognosing a neurodegenerative disorder in a subject, identifying a subject at risk of a neurodegenerative disorder, or prescribing a therapeutic regimen or predicting benefit from therapy in a subject having a neurodegenerative disorder based on the levels of the biomarker, wherein at least one of the one or more biomarkers are selected from the group consisting of low-density lipoprotein receptor-related protein 6 (LPR6), heat-shock factor-1 (HSF1), and repressor element 1-silencing transcription factor (REST). In some embodiments, the level of the one or more biomarkers in the biological sample is compared to the level of one or more biomarkers in a control sample and wherein the level of the one or more biomarkers of the biological sample is elevated compared to the control sample. In some embodiments, the level of the one or more biomarkers in the biological sample is compared to the level of one or more biomarkers in a control sample and wherein the level of the one or more biomarkers of the biological sample is decreased compared to the control sample. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In other embodiments, the method further comprises isolating vesicles from the biological samples. In other embodiments, the vesicles are selected from the group consisting of exosomes, microparticles, microvesicles, nanosomes, extracellular vesicles, and ectosomes. In other embodiments, the method further comprises isolating exosomes from the biological sample. In certain embodiments, the isolated exosomes are selected from the group consisting of neuron-derived exosomes, astrocyte-derived exosomes, oliogodendrocyte-derived exosomes, and microglia-derived exosomes. In other embodiments, the level of one or more biomarkers is the protein, mRNA, or miRNA level of the one or more biomarker. In some aspects, the methods of the present invention further comprise predicting the movement from preclinical to the manifestation of a neurodegenerative disorder. In other aspects, the methods of the present invention further comprise predicting outcome or worsening of the neurodegenerative disorder. In yet other aspects, the methods of the present invention comprise preventing Alzheimer's disease. In some aspects, the methods of the present invention further comprise predicting the conversion from mild cognitive impairment to Alzheimer's disease dementia. In other embodiments, the method further comprises measuring the level of one or more biomarkers in the biological sample, wherein at least one of the one or more biomarkers are selected from the group consisting of Tau, phosphorylated Tau, Aβ1-42, TDP-43, α-synuclein, SOD-1, FUS, FKBP51, IRS-1, phosphorylated IRS-1, cathepsin D (CTSD), type 1 lysosome-associated membrane protein (LAMP1), ubiquitinylated proteins (UBP), heat-shock protein 70 (HSP70), neuron-specific enolase (NSE), neurofilament light chain (NFL), CD9, CD63, CD81, and CD171.

The present invention also provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: isolating vesicles from a biological sample obtained from the subject; and determining the level of one or more biomarkers in the vesicles; wherein an elevated level of the one or more biomarkers in the sample compared to the level of the one or more biomarkers in a control sample is an indication of a neurodegenerative disorder, wherein at least one of the one or more biomarkers is selected from the group consisting of LRP6, HSF-1, and REST. In some embodiments, the level of the one or more biomarkers in the biological sample is decreased compared to the control sample. In other embodiments, the vesicles are selected from the group consisting of exosomes, microparticles, microvesicles, nanosomes, extracellular vesicles, and ectosomes. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In still other embodiments, the isolated exosomes are selected from the group consisting of neuron-derived exosomes, astrocyte-derived exosomes, oliogodendrocyte-derived exosomes, and microglia-derived exosomes. In other embodiments, the isolating vesicles from a biological sample comprises: contacting the biological sample with an agent under conditions wherein a vesicle present in said biological sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In other embodiments, the isolating vesicles from a biological sample comprises: isolating vesicles from said biological sample to obtain a vesicle sample; contacting the vesicle sample with an agent under conditions wherein a vesicle present in said vesicle sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In certain aspects, the agent is an antibody, a lectin, a ligand, a soluble receptor, a binding protein, or an oligonucleotide. In other aspects, the antibody is a polyclonal or monoclonal antibody. In yet other aspects, the antibody is a monoclonal NCAM antibody. In other aspects, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In other aspects, the antibody is a neuron-specific enolase antibody. In other aspects, the antibody is a monoclonal neuron-specific enolase antibody. In other embodiments, the vesicles are selected from the group consisting of exosomes, microparticles, microvesicles, nanosomes, extracellular vesicles, and ectosomes. In other embodiments, the level of one or more biomarkers is the protein, mRNA, or miRNA level of the one or more biomarker.

The present invention provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: obtaining a biological sample from the subject; applying an antibody specific for vesicles to the sample, wherein the presence of the vesicle creates an antibody-vesicle complex; isolating the antibody-vesicle complex; assaying a level of one or more biomarkers in the antibody-vesicle complex; and diagnosing or prognosing a neurodegenerative disorder in a subject, identifying a subject at risk of a neurodegenerative disorder, or prescribing a therapeutic regimen or predicting benefit from therapy in a subject having a neurodegenerative disorder based on the levels of the one or more biomarkers, wherein at least one of the biomarkers are selected from the group consisting of LRP6, HSF-1, and REST. In some embodiments, the antibody-vesicle complex is created on a solid phase. In yet other embodiments, the methods further comprise releasing the vesicle from the antibody-vesicle complex. In certain embodiments, the solid phase is non-magnetic beads, magnetic beads, agarose, or sepharose. In other embodiments, the vesicle is released by exposing the antibody-vesicle complex to low pH between 3.5 and 1.5. In yet other embodiments, the released vesicle is neutralized by adding a high pH solution. In other embodiments, the released vesicle is lysed by incubating the released vesicles with a lysis solution. In still other embodiments, the lysis solution contains inhibitors for proteases and phosphatases. In other embodiments, the levels of the one or more biomarkers are normalized by the number of vesicles or values of vesicle biomarkers. In other embodiments, the vesicles are selected from the group consisting of exosomes, microparticles, microvesicles, nanosomes, extracellular vesicles, and ectosomes. In certain embodiments, the antibody is a polyclonal or monoclonal antibody. In other embodiments, the antibody is a monoclonal NCAM antibody. In other embodiments, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In other aspects, the antibody is a neuron-specific enolase antibody. In other aspects, the antibody is a monoclonal neuron-specific enolase antibody. In some embodiments, the exosomes are selected from the group consisting of neuron-derived exosomes, astrocyte-derived exosomes, oliogodendrocyte-derived exosomes, and microglia-derived exosomes. In yet other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the level of one or more biomarkers is the protein, mRNA, or miRNA level of the one or more biomarker.

The present invention provides sets of biomarkers for assessing neurodegenerative disorder status of a subject comprising one or more biomarkers, wherein the levels of the biomarkers in the set are assayed; and wherein the biomarker level determines the neurodegenerative disorder status of the subject with at least 40% specificity, wherein the at least one or more of the set of biomarkers are selected from the group consisting of LRP6, HSF-1, and REST. In some embodiments, the biomarker level determines the neurodegenerative disorder status of the subject with at least 40%, 50%, 60%, 70%, 75%, 80%, 85%, 90%, 95%, 99%, or 100% specificity. In some embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In yet other embodiments, the methods further comprise assaying the levels of the biomarkers in vesicles from the sample. In other embodiments, the vesicles are selected from the group consisting of exosomes, microparticles, microvesicles, nanosomes, extracellular vesicles, and ectosomes. In other embodiments, the sets of biomarkers of the present invention further comprise one or more biomarkers selected from the group consisting of Tau, phosphorylated Tau, Aβ1-42, TDP-43, α-synuclein, SOD-1, FUS, FKBP51, IRS-1, phosphorylated IRS-1, cathepsin D (CTSD), type 1 lysosome-associated membrane protein (LAMP1), ubiquitinylated proteins (UBP), heat-shock protein 70 (HSP70), neuron-specific enolase (NSE), neurofilament light chain (NFL), CD9, CD63, CD81, and CD171.

The present invention also provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, the kit comprising one or more agents which specifically binds vesicles, one or more agents which specifically bind a biomarker, one or more containers for collecting and or holding the biological sample, and an instruction for its use, wherein the neurodegenerative disorder is associated with altered biomarker levels and wherein the biomarker is selected from the group consisting of LRP6, HSF-1, and REST. In other embodiments, the vesicles are selected from the group consisting of exosomes, microparticles, microvesicles, nanosomes, extracellular vesicles, and ectosomes. In some embodiments, the agents are polyclonal or monoclonal antibodies. In other embodiments, the antibodies are a monoclonal NCAM antibody. In other embodiments, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In other aspects, the antibody is a neuron-specific enolase antibody. In other aspects, the antibody is a monoclonal neuron-specific enolase antibody. In certain embodiments, the exosomes are selected from the group consisting of neuron-derived exosomes, astrocyte-derived exosomes, oliogodendrocyte-derived exosomes, and microglia-derived exosomes. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In yet other embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the kits further comprise a computer model or algorithm for analyzing the biomarker level in the sample.

The present invention also provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, the kit comprising one or more agents which specifically binds vesicles, one or more probes or primers for detecting biomarker mRNA or miRNA, one or more containers for collecting and or holding the biological sample, and an instruction for its use, wherein the neurodegenerative disorder is associated with altered biomarker levels and wherein the biomarker is selected from the group consisting of LRP6, HSF-1, and REST. In other embodiments, the vesicles are selected from the group consisting of exosomes, microparticles, microvesicles, nanosomes, extracellular vesicles, and ectosomes. In some embodiments, the agents are polyclonal or monoclonal antibodies. In other embodiments, the exosomes are selected from the group consisting of neuron-derived exosomes, astrocyte-derived exosomes, oliogodendrocyte-derived exosomes, and microglia-derived exosomes. In yet other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In still other embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the kits further comprise a computer model or algorithm for analyzing the biomarker level in the sample. In some embodiments, the kits of the present invention further comprise one or more agents which specifically bind to one or more biomarkers selected from the group consisting of Tau, phosphorylated Tau, Aβ1-42, TDP-43, α-synuclein, SOD-1, FUS, FKBP51, IRS-1, phosphorylated IRS-1, cathepsin D (CTSD), type 1 lysosome-associated membrane protein (LAMP1), ubiquitinylated proteins (UBP), heat-shock protein 70 (HSP70), neuron-specific enolase (NSE), neurofilament light chain (NFL), CD9, CD63, CD81, and CD171.

In other embodiments, the present invention provides methods of diagnosing a neurodegenerative disorder in a subject, comprising the steps of: (i) obtaining a test biological sample containing vesicles from the subject, (ii) measuring the level of one or more biomarkers in the test biological sample, (iii) comparing the level of the one or more biomarkers in the test biological sample to a control level of the one or more biomarkers in a control biological sample, and (iv) determining the subject has a neurodegenerative disorder by detecting an increased or decreased level of the one or more biomarkers in the test biological sample, relative to the control biological sample, wherein at least one of the one or more biomarkers is selected from the group consisting of LRP6, HSF-1, and REST. In other embodiments, the vesicles are selected from the group consisting of exosomes, microparticles, microvesicles, nanosomes, extracellular vesicles, and ectosomes. In some embodiments, the exosomes are selected from the group consisting of neuron-derived exosomes, astrocyte-derived exosomes, oliogodendrocyte-derived exosomes, and microglia-derived exosomes. In yet other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In still other embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the method further comprises isolating vesicles from the biological sample. In other embodiments, the vesicles are selected from the group consisting of exosomes, microparticles, microvesicles, nanosomes, extracellular vesicles, and ectosomes. In some embodiments an increase in the level of one or more biomarkers of the present invention is indicative of a first neurodegenerative disorder and a decrease in the level of the same one or more biomarkers is indicative of a second neurodegenerative disorder.

In other embodiments, the present invention provides methods for analyzing a sample from a subject comprising the steps of: (i) obtaining a biological sample comprising vesicles from the subject, (ii) measuring the level of one or more biomarkers in the biological sample, and (iii) comparing the level of the one or more biomarkers in the biological sample to a control level of the one or more biomarkers in a control biological sample. In some embodiments, the subject has been diagnosed or suspected of having a neurodegenerative disorder. In other embodiments, the method further comprises diagnosing or prognosing a neurodegenerative disorder in the subject, identifying risk of a neurodegenerative disorder in the subject, or prescribing a therapeutic regimen or predicting benefit from therapy for the subject having or suspected of having a neurodegenerative disorder. In certain embodiments, at least one of the one or more biomarkers are selected from the group consisting of LRP6, HSF-1, and REST. In some embodiments, the level of the one or more biomarkers in the biological sample is compared to the level of one or more biomarkers in a control sample and wherein the level of the one or more biomarkers of the biological sample is elevated compared to the control sample. In some embodiments, the level of the one or more biomarkers in the biological sample is compared to the level of one or more biomarkers in a control sample and wherein the level of the one or more biomarkers of the biological sample is decreased compared to the control sample. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In other embodiments, the method further comprises isolating vesicles from the biological samples. In other embodiments, the vesicles are selected from the group consisting of exosomes, microparticles, microvesicles, nanosomes, extracellular vesicles, and ectosomes. In other embodiments, the method further comprises isolating exosomes from the biological sample. In certain embodiments, the isolated exosomes are selected from the group consisting of neuron-derived exosomes, astrocyte-derived exosomes, oliogodendrocyte-derived exosomes, and microglia-derived exosomes. In other embodiments, the methods of the present invention further comprise a computer model or algorithm for analyzing the one or more biomarker level in the sample. In other embodiments, the level of one or more biomarkers is the protein, mRNA, or miRNA level of the one or more biomarker.

In other embodiments, the present invention provides methods for diagnosing or prognosing a neurodegenerative disorder in a subject, comprising the steps of: (a) providing a sample comprising vesicles obtained from a subject; (b) assessing the level of one or more biomarkers comprising LRP6, HSF-1, and REST in the sample; (c) comparing the LRP6, HSF-1, and/or REST levels in the sample with LRP6, HSF-1, and/or REST levels in a normal control; and (d) determining whether the subject has or is likely to have a neurodegenerative disorder in accordance with the result of step (c). In certain aspects, a subject with LRP6, HSF-1, and REST levels in the sample that are lower than those in the normal control has or is likely to have Alzheimer's disease. In other aspects, a subject with REST levels in the sample that are higher than those in the normal control has or is likely to have frontotemporal dementia (FTD). In one embodiment, the level of LRP6, HSF-1 and REST is assessed by ELISA. In other embodiments, the method further comprises isolating vesicles from the biological sample. In certain embodiments, the vesicles are selected from the group consisting of exosomes, microparticles, microvesicles, nanosomes, extracellular vesicles, and ectosomes.

In other embodiments, the invention provides for a method of diagnosing, prognosing, determining, predicting a therapeutic regimen or predicting benefit from therapy for a neurodegenerative disorder, comprising assaying a biomarker level in a sample from the subject for a plurality of biomarkers, wherein the plurality of biomarkers comprises one or more biomarkers selected from LRP6, HSF-1, and REST; and diagnosing, prognosing, determining progression of the neurodegenerative disorder, predicting a therapeutic regimen or predicting benefit from therapy in a subject having a neurodegenerative disorder based on the levels of the plurality of biomarkers. In one aspect, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the method further comprises assaying the level of one or more biomarkers in the biological sample, wherein at least one of the one or more biomarkers are selected from the group consisting of Tau, phosphorylated Tau, Aβ1-42, TDP-43, α-synuclein, SOD-1, FUS, FKBP51, IRS-1, phosphorylated IRS-1, cathepsin D (CTSD), type 1 lysosome-associated membrane protein (LAMP1), ubiquitinylated proteins (UBP), heat-shock protein 70 (HSP70), neuron-specific enolase (NSE), neurofilament light chain (NFL), CD9, CD63, CD81, and CD171.

In another embodiment, the present invention provides a method of diagnosing and treating a neurodegenerative disorder in a subject, said method comprising: (a) obtaining a sample from a subject, wherein the sample comprises vesicles; (b) processing the sample to isolate or enrich the sample for the vesicles containing biomarkers; and (c) detecting the level of one or more biomarkers in said vesicles, (d) diagnosing the subject with a neurodegenerative disorder based on the level of the one or more biomarkers in the sample relative to the level in a control sample; and (e) administering an effective amount of a therapeutic agent to the diagnosed subject. In one aspect, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the method further comprises assaying the level of one or more biomarkers in the biological sample, wherein at least one of the one or more biomarkers are selected from the group consisting of Tau, phosphorylated Tau, Aβ1-42, TDP-43, α-synuclein, SOD-1, FUS, FKBP51, IRS-1, phosphorylated IRS-1, cathepsin D (CTSD), type 1 lysosome-associated membrane protein (LAMP1), ubiquitinylated proteins (UBP), heat-shock protein 70 (HSP70), neuron-specific enolase (NSE), neurofilament light chain (NFL), CD9, CD63, CD81, and CD171. In some embodiments, the vesicles are exosomes. In other embodiments, the exosomes are neuron-derived exosomes, astrocyte-derived exosomes, oliogodendrocyte-derived exosomes, or microglia-derived exosomes.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

DESCRIPTION OF THE INVENTION

Figure 1:
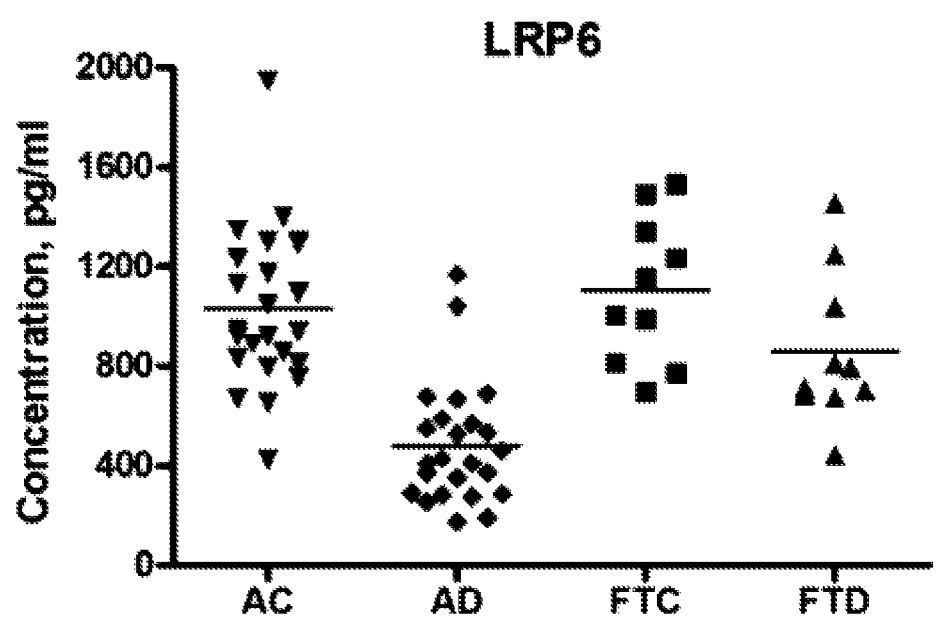
FIG. 1 sets forth data showing levels of neural-derived plasma exosomal proteins in patients with Alzheimer's disease, frontotemporal dementia, and matched cognitively normal case controls.

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the discovery that exosomal biomarkers can be assayed to identify subjects having or likely to develop neurodegenerative disorders, including, for example, Alzheimer's disease (AD), multiple sclerosis (MS), and frontotemporal dementia (FTD).

The present invention is based, in part, on the discovery of unexpected increases in certain biomarkers in neuron-derived exosomes present in the circulation of subjects having neurodegenerative disease (e.g., Alzheimer's disease). The present invention demonstrates that exosomal levels of these biomarkers may be assayed to diagnose a neurodegenerative disorder in a subject having a neurodegenerative disease. The present invention further shows that measurement of certain biomarkers in neuron-derived exosomes from a subject may be used to predict the subsequent development of a neurodegenerative disease (e.g., identify a subject at risk of developing a neurodegenerative disorder).

The present invention also provides compositions for use in the methods described herein. Such compositions may include small molecule compounds; peptides and proteins including antibodies or functionally active fragments thereof; and polynucleotides including small interfering ribonucleic acids (siRNAs), micro-RNAs (miRNAs), ribozymes, and anti-sense sequences. (See, e.g., Zeng (2003) Proc Natl Acad Sci USA 100:9779-9784; and Kurreck (2003) Eur J Biochem 270:1628-1644.)

The present invention further provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder. In these embodiments, the kits comprise one or more antibodies which specifically binds exosomes, one or more antibodies which specifically bind a biomarker, one or more containers for collecting and or holding the biological sample, and an instruction for the kits use.

The section headings are used herein for organizational purposes only, and are not to be construed as in any way limiting the subject matter described herein.

Biological Sample

The present invention provides biomarkers and diagnostic and prognostic methods for Alzheimer's disease and other neurodegenerative disorders. Biomarkers levels are determined in a biological sample obtained from a subject. In some embodiments, the biological sample of the invention can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Biological samples can also be obtained from other sources known in the art, including whole blood, serum, plasma, urine, interstitial fluid, peritoneal fluid, cervical swab, tears, saliva, buccal swab, skin, cerebrospinal fluid, or other tissues including, for example, brain tissues.

Enrichment or Isolation of Vesicles (Exosomes, Microparticles, Microvesicles, Nanosomes, Extracellular Vesicles, and Ectosomes)

Samples can be enriched for vesicles through positive selection, negative selection, or a combination of positive and negative selection. In some embodiments, vesicles are directly captured. In other embodiments, blood cells are captured and vesicles are collected from the remaining biological samples. In some embodiments, the vesicles enriched in the biological samples are exosomes, microparticles, microvesicles, nanosomes, extracellular vesicles, or ectosomes. In some embodiments, the vesicles enriched in the biological samples are neuron-derived exosomes, astrocyte-derived exosomes, oliogodendrocyte-derived exosomes, and microglia-derived exosomes.

Samples can also be enriched for vesicles based on differences in the biochemical properties of vesicles. For example, samples can be enriched for vesicles based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used. In some of the embodiments based on metabolic differences, dye uptake/exclusion measured by flow cytometry or another sorting technology is used. In some of the embodiments based on gene expression, cell culture with cytokines is used. Samples can also be enriched for vesicles based on other biochemical properties known in the art. For example, samples can be enriched for vesicles based on pH or motility. Further, in some embodiments, more than one method is used to enrich for vesicles. In other embodiments, samples are enriched for vesicles using antibodies, ligands, or soluble receptors.

In other embodiments, surface markers are used to positively enrich vesicles in the sample. In some embodiments, the vesicles are exosomes, microparticles, microvesicles, nanosomes, extracellular vesicles, or ectosomes. In other embodiments, NCAM, CD171, CD9, CD63, CD81, neuron-specific enolase, diverse neuron or astrocyte adhesive proteins, microglial CD18/11, or CD3 T cell membrane cell surface markers are used to enrich for exosomes. In some embodiments, cell surface markers that are not found on vesicles populations are used to negatively enrich vesicles by depleting cell populations. Flow cytometry sorting may also be used to further enrich for exosomes using cell surface markers or intracellular or extracellular markers conjugated to fluorescent labels. Intracellular and extracellular markers may include nuclear stains or antibodies against intracellular or extracellular proteins preferentially expressed in vesicles. Cell surface markers may include antibodies against cell surface antigens that are preferentially expressed on exosomes (e.g., NCAM). In some embodiments, the cell surface marker is a neuron-derived exosome surface marker, including, for example, NCAM or CD171. In some embodiments, a monoclonal NCAM, CD9, CD63, CD81, neuron-specific enolase or CD171 antibody is used to enrich or isolate exosomes from the sample. In certain aspects, the NCAM, CD9, CD63, CD81, neuron-specific enolase or CD171 antibody is biotinylated. In this embodiment, biotinylated NCAM or CD171 antibody can form an antibody-exosome complex that can be subsequently isolated using streptavidin-agarose resin or beads. In other embodiments, the NCAM, CD9, CD63, CD81, neuron-specific enolase or CD171 antibody is a monoclonal anti-human NCAM, CD9, CD63, CD81, neuron-specific enolase or CD171 antibody.

In some embodiments, enriched vesicles from the biological sample are subsequently enriched for a specific type of vesicle. For example, the biological sample is enriched for exosomes and then the enriched exosomes are subsequently enriched for neural-derived exosomes. In some embodiments, the biological sample is enriched for individual neural cell sources of vesicles. In certain aspects, the neural cell sources of vesicles are microglia, neurons, or astrocytes.

In other embodiments, vesicles are isolated or enriched from a biological sample comprising: contacting a biological sample with an agent under conditions wherein a vesicle present in said biological sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In certain embodiments, the agent is an antibody or a lectin. Lectins useful for forming a vesicle-lectin complex are described in U.S. Patent Application Publication No. 2012/0077263. In some embodiments, the vesicle is an exosome, a microparticle, a microvesicle, nanosomes, extracellular vesicles, or an ectosome. In some embodiments, the exosomes are neuron-derived exosomes, astrocyte-derived exosomes, oliogodendrocyte-derived exosomes, or microglia-derived exosomes. In some embodiments, multiple isolating or enriching steps are performed. In certain aspects of the present embodiment, a first isolating step is performed to isolate exosomes from a blood sample and a second isolating step is performed to isolate neural-derived exosomes from other exosomes. In other embodiments, the vesicle portion of the vesicle-agent complex is lysed using a lysis reagent and the protein levels of the lysed vesicle are assayed. In some embodiments, the antibody-vesicle complex is created on a solid phase. In yet other embodiments, the methods further comprise releasing the vesicle from the antibody-vesicle complex. In certain embodiments, the solid phase is non-magnetic beads, magnetic beads, agarose, or sepharose. In other embodiments, the vesicle is released by exposing the antibody-vesicle complex to low pH between 3.5 and 1.5. In yet other embodiments, the released vesicle is neutralized by adding a high pH solution. In other embodiments, the released vesicle is lysed by incubating the released vesicles with a lysis solution. In still other embodiments, the lysis solution contains inhibitors for proteases and phosphatases.

Neurodegenerative Disorders

The present invention provides methods for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder.

In some embodiments the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

In some embodiments, the present invention enables a medical practitioner to diagnose or prognose one or more neurodegenerative disorder in a subject. In other embodiments, the present invention enables a medical practitioner to rule out or eliminate one or more neurodegenerative diseases as a diagnostic possibility. In yet other embodiments, the present invention enables a medical practitioner to identify a subject at risk of developing a neurodegenerative disorder. In other embodiments, the present invention enables a medical practitioner to predict whether a subject will later develop a neurodegenerative disorder. In further embodiments the present invention enables a medical practitioner to prescribe a therapeutic regimen or predict benefit from therapy in a subject having a neurodegenerative disorder.

Biomarkers

Biomarker levels are assayed in a biological sample obtained from a subject having or at-risk of having a neurodegenerative disorder (e.g., Alzheimer's disease). In some embodiments, the biomarker is LRP6, HSF-1, or REST. Other known neurodegenerative disorder biomarkers may be used in combination with the biomarkers of the present invention. Examples of such biomarkers are provided in US Patent Application Pub. No. 2015/0119278, the contents of which are hereby incorporated by reference.

In some embodiments, biomarker levels of the present invention are measured by determining the gene expression of the biomarker. In certain embodiments, gene expression changes are measured by determining the expression level of one or more of the genes shown in Table 1. La certain aspects, gene expression of the biomarker is determined using PCR, microarray, sequencing. In some embodiments, the expression level of the biomarker is determined by measuring the mRNA or miRNA level of the biomarker.

One of ordinary skill in the art has several methods and devices available for the detection and analysis of the markers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of neurodegenerative disorders (e.g., Alzheimer's disease). Markers of such disorders are typically substances found in a bodily sample that can be measured. The measured amount can correlate to underlying disorder or disease pathophysiology, presence or absence of a neurodegenerative disorder, probability of a neurodegenerative disorder in the future. In patients receiving treatment for their condition the measured amount will also correlate with responsiveness to therapy. In some embodiments an increase in the level of one or more biomarkers of the present invention is indicative of a first neurodegenerative disorder and a decrease in the level of the same one or more biomarkers is indicative of a second neurodegenerative disorder. For example, an increase in REST levels is indicative of frontotemporal dementia whereas a decrease in REST levels is indicative of Alzheimer's disease. Accordingly, the methods of the present invention are useful for the differential diagnosis of neurodegenerative disorders.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present invention may be used in clinical assays to diagnose or prognose a neurodegenerative disorder in a subject, identify a subject at risk of a neurodegenerative disorder, and/or for prescribing a therapeutic regimen or predicting benefit from therapy in a subject having a neurodegenerative disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a neurodegenerative disorder in a subject, identifying a subject at risk of a neurodegenerative disorder, or for prescribing a therapeutic regimen or predicting benefit from therapy in a subject having a neurodegenerative disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 100%.

Compositions

Compositions useful in the methods of the present invention include compositions that specifically recognize a biomarker associated with a neurodegenerative disorder, wherein the biomarker is LRP6, HSF-1, and REST. In yet other embodiments, the composition is selected from the group consisting of a peptide, a nucleic acid, an antibody, and a small molecule.

In certain embodiments, the present invention relates to compositions that specifically detect a biomarker associated with a neurodegenerative disorder. As detailed elsewhere herein, the present invention is based upon the finding that LRP6, HSF-1, and REST are specific biomarkers for AD and other neurodegenerative disorders. In some embodiments, the compositions of the present invention specifically bind to and detect LRP6, HSF-1, and REST.

In some embodiments, the composition comprises an antibody, where the antibody specifically binds to a biomarker or vesicles of the invention. The term "antibody" as used herein and further discussed below is intended to include fragments thereof which are also specifically reactive with a biomarker or vesicle (e.g., exosome). Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', $F(ab')_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an exosome or a biomarker of the present invention, including, for example, neuron-derived exosome, LRP6, HSF-1, and REST.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a neurodegenerative disorder. As detailed elsewhere herein, the present invention is based upon the findings that LRP6, HSF-1, and REST levels are implicated in the pathology of a variety of neurodegenerative disorders, such as, for example, Alzheimer's disease. Therefore, in one embodiment, the present invention provides compositions that prevent decreases in LRP6, HSF-1, or REST levels. In other embodiments, the compositions prevent increases in LRP6, HSF-1, or REST levels. In one embodiment, the compositions reduce LRP6, HSF-1, or REST levels. In yet other embodiments, the compositions increase LRP6, HSF-1, or REST levels.

Methods of Treatment

The present invention provides methods of treating a neurodegenerative disorder in a subject, comprising administering to the subject an effective amount of a composition, wherein the composition reduces the level of LRP6, HSF-1, or REST. In other embodiments, the composition increases the levels of LRP6, HSF-1, or REST. In yet other embodiments, the composition prevents decreases in LRP6, HSF-1, or REST levels. In still other embodiments, the composition prevents increases in LRP6, HSF-1, or REST levels. In other embodiments, the present invention provides methods of treating a neurodegenerative disorder in a subject, comprising administering to the subject an effective amount of a composition, wherein the composition normalizes the level of LRP6, HSF-1, and REST to a reference level.

Kits

Another aspect of the invention encompasses kits for detecting or monitoring a neurodegenerative disorder in a subject. A variety of kits having different components are contemplated by the current invention. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating exosomes in a biological sample. In further aspects, the means for enriching or isolating exosomes comprises reagents necessary to enrich or isolate exosomes from a biological sample. In certain aspects, the kit comprises a means for quantifying the amount of a biomarker. In further aspects, the means for quantifying the amount of a biomarker comprises reagents necessary to detect the amount of a biomarker.

TABLE 1

| Gene | Entrez Gene Name | Location |
|---|---|---|
| low density lipoprotein receptor-related protein 6 | LRP6 | Chromosome 12 - NC_000012.12 (12116025 ... 12267007) |
| heat shock transcription factor 1 | HSF1 | NC_000008.11 (144291588 ... 144314722) |
| Repressor Element 1-silencing transcription factor | REST | NC_000004.12 (56907876 ... 56935845) |

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1

Neuron-Derived Plasma Exosomal LRP6, HSF1 and REST Levels in Human Subjects with Alzheimer's Disease Levels of LRP6, HSF1 and REST protein were assayed in human subjects with Alzheimer's disease (AD) as follows. Venous blood was collected from control subjects (AC, n=24) and subjects with AD (n=24). AD subjects were further classified as having mild cognitive impairment (MCI, n=16) or dementia (n=8). The diagnosis of AD, MCI, and dementia was established by standard clinical and laboratory criteria.

For blood collection, 30 ml of venous blood were drawn into 100 U/ml of heparin and centrifuged for 15 min at 2000 g. Plasmas were stored in 0.5 ml aliquots at −80° C.

For plasma, 250 ul received 0.1 ml of thromboplastin-D (Fisher Scientific, Inc., Hanover Park, Ill.) followed by addition of 0.15 ml of calcium- and magnesium-free DBS containing 3-times the recommended concentrations of protease and phosphatase inhibitor cocktails.

ExoQuick (EXOQ; System Biosciences, Inc., Mountain View, Calif.) was added to 3000 g supernates to precipitate total exosomes that were re-suspended for immunochemical enrichment of exosomes from neural sources.

Exosomes absorbed by mouse anti-human CD171 (L1CAM) biotinylated antibody (clone 5G3, eBioscience, San Diego, Calif.) and Streptavidin-Plus Ultralink resin (Pierce-Thermo Scientific, Inc.) were released into 50 ul of 0.05 mol/L acetic acid (pH 2.5) followed by addition to 3000 g supernates of 42 ul of 3% bovine serum albumin (BSA), 8 ul of 1 mol/L Tris-HCl (pH 8.0) and 0.40 ml of M-PER mammalian protein extraction reagent (Thermo Scientific).

Neural exosomal proteins neuron-specific enolase (NS-enolase) (R&D Systems, Minneapolis, Minn.), type 1 neural cell adhesion molecule (NCAM-1) (Raybiotech, Norcross, Ga.) and tetraspanning exosome marker human CD81 (Cusabio-American Research Products, Waltham, Mass.) were quantified in the linear range of ELISAs. Transcription factors were quantified by ELISAs for HSF1 (Enzo Life Sciences, Farmingdale, N.Y.), REST (Cusabio, American Research Products) and LRP6 (USCN Life Science, American Research Products). Neural exosomal levels of CD-81 showed similar amount of exosomes between control and AD samples (data not shown).

Figure 2:
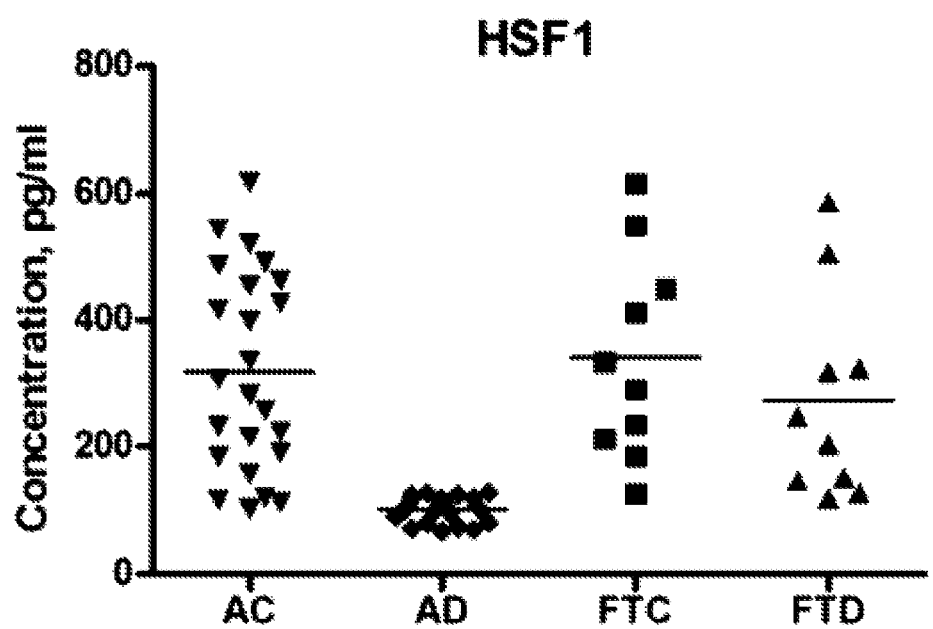
FIG. 2 sets forth data showing levels of neural-derived plasma exosomal proteins in patients with Alzheimer's disease, frontotemporal dementia, and matched cognitively normal case controls.
Figure 3:
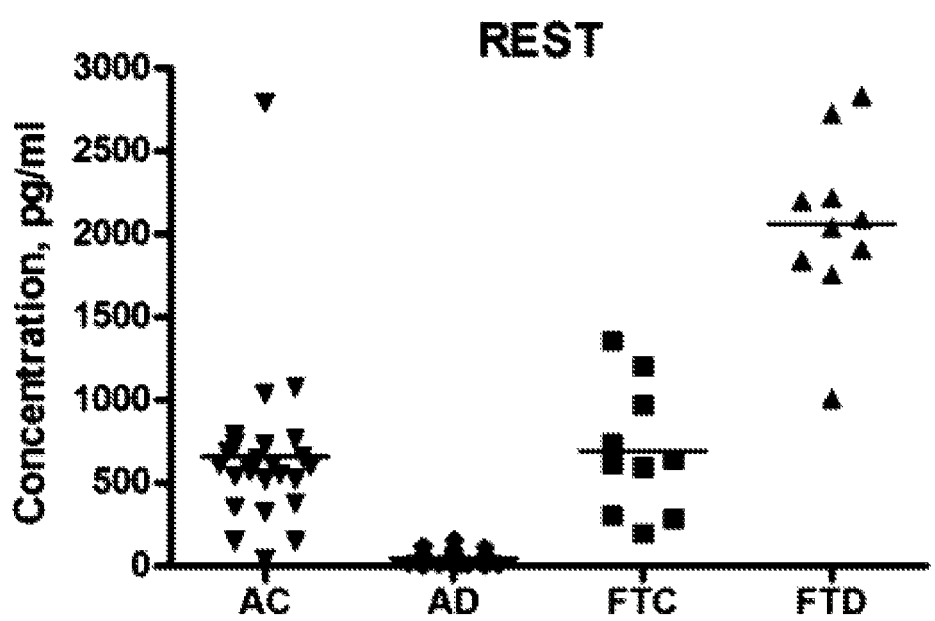
FIG. 3 sets forth data showing levels of neural-derived plasma exosomal proteins in patients with Alzheimer's disease, frontotemporal dementia, and matched cognitively normal case controls.
Figure 4:
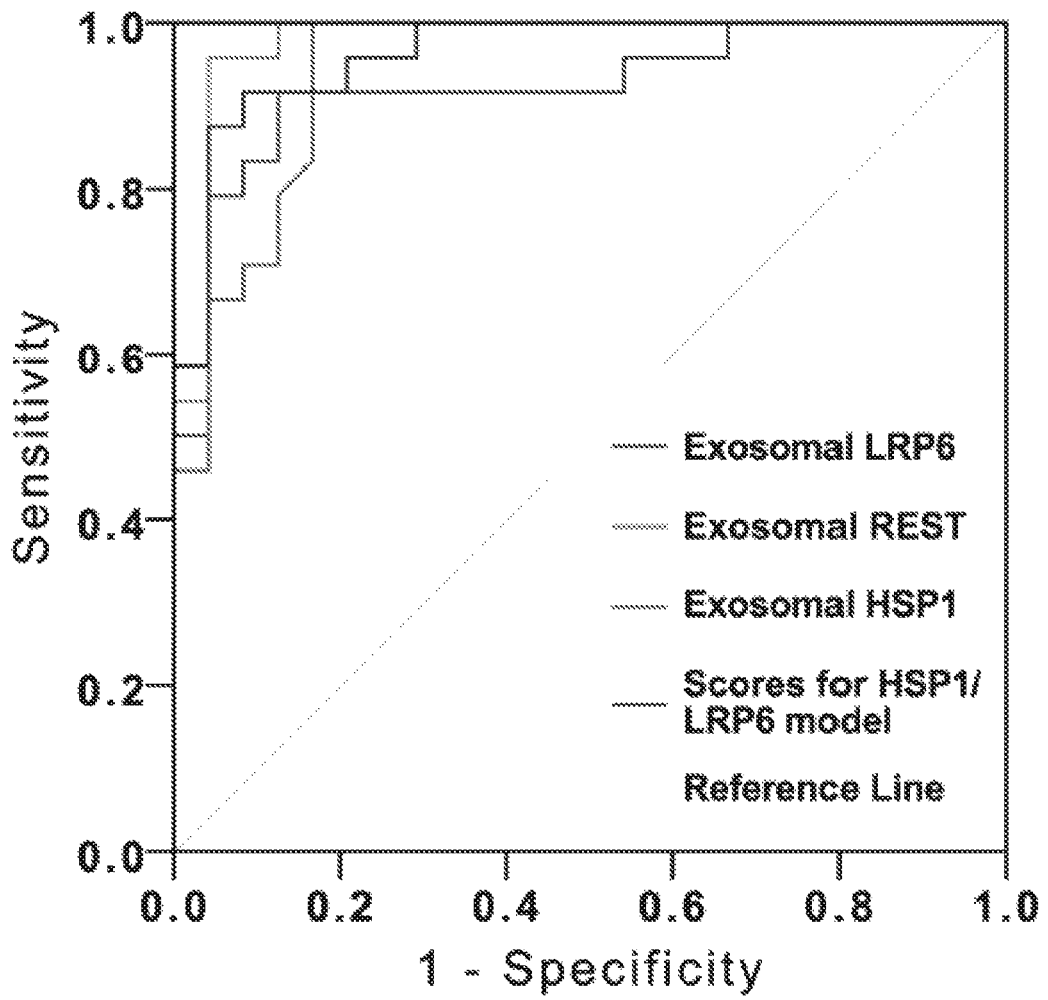
FIG. 4 sets forth data showing ROC plots depicting distinctions between Alzheimer's disease and matched cognitively normal case controls.

Transcription factor levels of plasma neural exosomes were significantly lower in subjects with AD compared to control subject plasma exosomal levels (see FIGS. 1-3). The mean±SEM levels of LRP6, HSF1, and REST for AD patients (483±49.9, 102±3.96, and 47.4±8.16 pg/ml) were significantly lower than those for AC controls (1028±64.7, 319±32.0, and 667±140 pg/ml) (all p<0.0001). As shown in Table 1 below, there were no differences between levels of the transcription factors in AD patients with MCI and those with dementia. ROC analyses of all analytes correctly classified 79% of AC subjects and 92% of AD patients as having primary pathogenic proteins (see FIG. 4).

TABLE 1

| Group | LRP6 (pg/ml) | HSF1 (pg/ml) | REST (pg/ml) |
|---|---|---|---|
| AD, MCI (n = 16) | 454 ± 55.1 | 102 ± 4.95 | 51.8 ± 10.5 |
| AD, dementia (n = 8) | 539 ± 104 | 101 ± 7.73 | 38.6 ± 13.1 |

All values are Mean ± SEM.

These results showed that neuron-derived plasma exosomal levels of LRP6, HSF1, and REST are useful for identifying subjects with AD. These results further indicated that methods and biomarkers of the present invention are useful for diagnosing Alzheimer's disease and other neurodegenerative disorders.

Example 2

Neuron-Derived Serum Exosomal Protein Levels in Human Subjects with Frontotemporal Dementia Another series of experiments were carried out to determine the levels of LRP6, HSF1 and REST protein in human subjects with frontotemporal dementia (FTD). Venous blood was collected from control subjects (FTC, n=10) and subjects with FTD (n=10). FTD subjects were further classified as having mild dementia (n=6) or moderate dementia (n=6). The diagnosis of FTD and dementia was established by standard clinical and laboratory criteria.

Blood collection and sample processing were performed as described above in Example 1 and neuron-derived exosomal protein levels for LRP6, HSF1 and REST were quantified using the ELISA kits described above in Example 1.

As shown in FIG. 3, REST levels were significantly higher for FTD patients (2065±162 pg/ml) than FTC controls (691±123 pg/ml) (p<0.0001). There were no significant differences in LRP6 or HSF1 between the FTD (857±96.2 and 274±51.0 pg/ml) and FTC (1104±94 and 341±51.4 pg/ml) groups (see FIGS. 1 and 2).

These results showed that neuron-derived serum exosomal levels of REST are useful for identifying subjects with FTD. These results further indicated that methods and compositions of the present invention are useful for diagnosing frontotemporal dementia and other neurodegenerative disorders.

Example 3

Neuron-Derived Plasma Exosomal LRP6, HSF1, and REST Levels Predict Development of Alzheimer's Disease in Human Subjects Exosomal levels of LRP6, HSF1, and REST protein levels were assayed in human subjects as follows. Thirty milliliters of venous blood were collected from subjects (n=16) at two time-points: the first at two to ten years before the subjects' diagnosis of Alzheimer's disease (Alzheimer's preclinical, AP) and the second at the time of initial diagnosis of Alzheimer's disease (AD). Venous blood samples were also collected from control subjects (n=16). Blood samples were processed and exosomes were isolated as described in Example 1 above.

Exosome proteins LRP6, HSF1, and REST were quantified by ELISA kits as described in Example 1.

Figure 5:
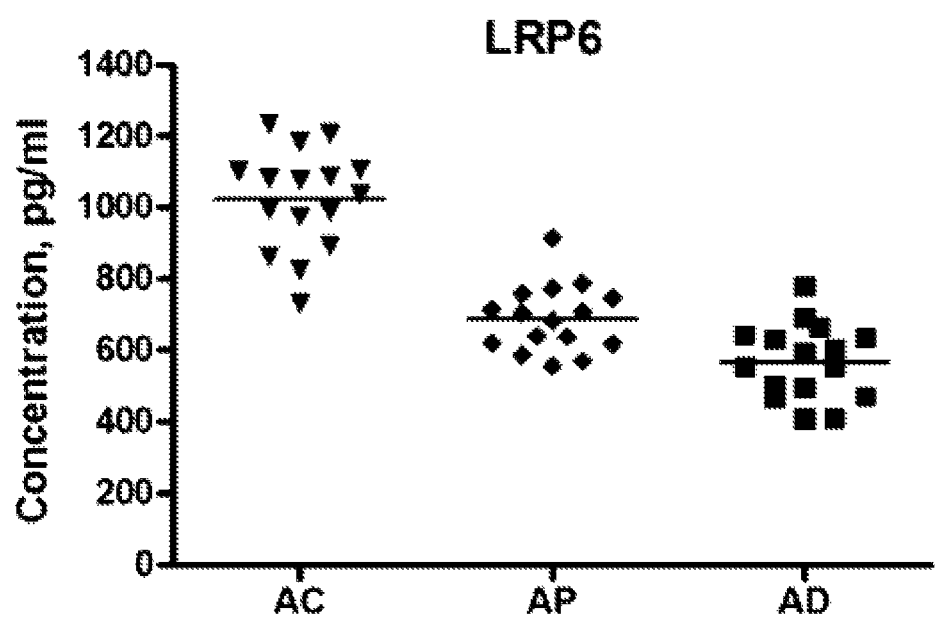
FIG. 5 sets forth data showing sequential levels of neural-derived plasma exosomal proteins in patients with Alzheimer's disease measured first at a time of normal cognition and later at the time of development of MCI or dementia.
Figure 6:
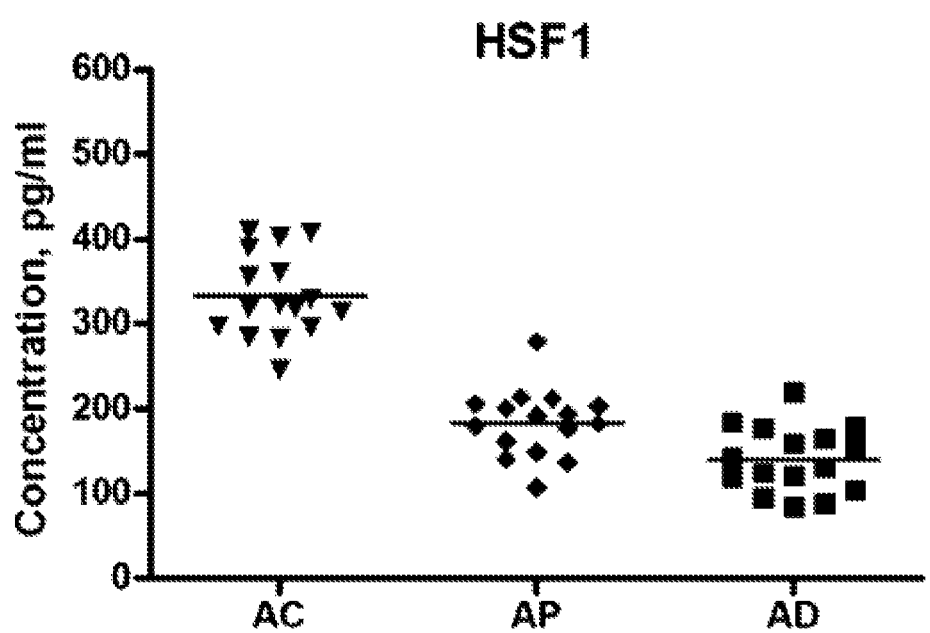
FIG. 6 sets forth data showing sequential levels of neural-derived plasma exosomal proteins in patients with Alzheimer's disease measured first at a time of normal cognition and later at the time of development of MCI or dementia.
Figure 7:
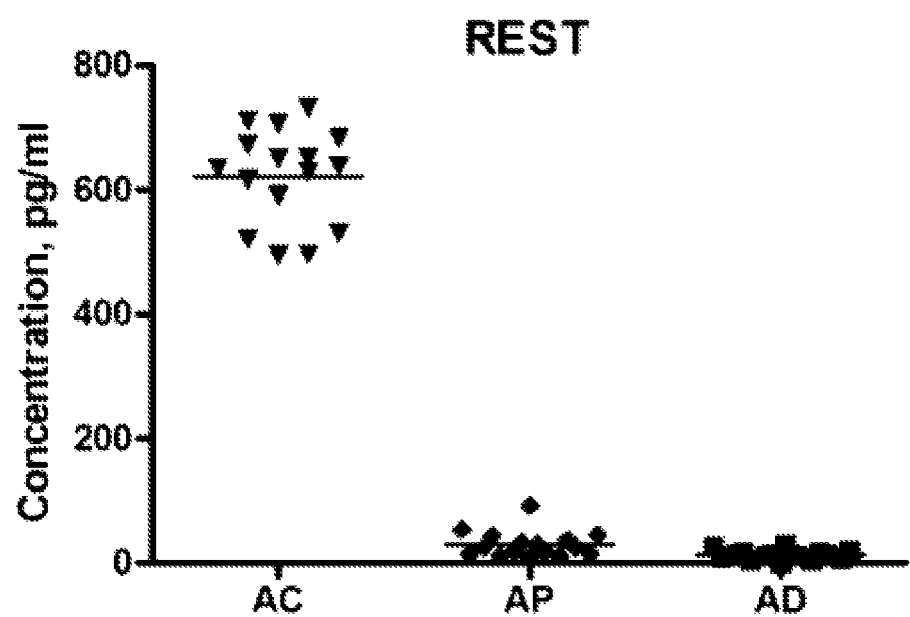
FIG. 7 sets forth data showing sequential levels of neural-derived plasma exosomal proteins in patients with Alzheimer's disease measured first at a time of normal cognition and later at the time of development of MCI or dementia.

As shown in FIGS. 5-7, neuron-derived plasma exosomal LRP6, HSF1, and REST levels for AD patients 2-10 years before (AP) and at the time of diagnosis (AD) were significantly lower than for AC control subjects. The mean±SEM levels of LRP6, HSF1, and REST for the AD group (568±263, 140±9.75, and 13.8±1.87 pg/ml) and for the AP group (689±23.6, 183±9.95, and 30.7±5.37 pg/ml) were significantly lower than those for AC controls (1028±64.7, 319±32.0, and 667±140 pg/ml) (all p<0.0001). The levels for the AD group all were significantly lower than those for the AP group (see FIGS. 5-7). Thus, levels of these transcription factors were significantly low for years before appearance of clinical signs of AD and there was continued declination with time.

These results showed that neuron-derived plasma exosomal levels of LRP6, HSF1, and REST are lower in subjects with Alzheimer's disease and are useful for identifying subjects with Alzheimer's disease. These results also showed that neuron-derived plasma exosomal levels of LRP6, HSF1, and REST are lower in subjects as early as 10 years before clinical diagnosis of Alzheimer's disease. These results further showed that assays and methods of the present invention are useful for identifying a subject at risk of a neurodegenerative disorder (e.g., Alzheimer's disease). Additionally, these results showed that the assays and methods of the present invention may be useful for early detection and determining the progression of Alzheimer's disease. These results further indicated that methods and compositions of the present invention are useful for diagnosing Alzheimer's disease and other neurodegenerative disorders.

Example 4

Neuron-Derived Plasma Exosomal REST Levels Predict Conversion from Mild Cognitive Impairment to Alzheimer's Disease in Human Subjects Neuron-derived exosomal levels of REST protein were assayed in human subjects for prediction and staging of mild cognitive impairment (MCI) and Alzheimer's disease (AD) as follows. Sixty plasma samples were acquired through the Alzheimer's Disease Cooperative Study (ADCS) Biomarker Core at University of California, San Diego (UCSD). Four clinical cohorts were identified: cognitively normal controls (CNC, n=10); patients with an established diagnosis of mild to moderate AD (AD, n=10), patients with stable mild cognitive impairment (MCI; n=20), and patients who transitioned within 36 months from MCI to AD (ADC, n=20).

Two hundred-fifty μL of plasma were incubated with thromboplastin-D (Fisher Scientific, Inc., Hanover Park, Ill.) followed by addition of calcium- and magnesium-free Dulbecco's balanced salt solution ($DBS^{-2}$) with protease inhibitor cocktail (Roche Applied Sciences, Inc., Indianapolis, Ind.) and phosphatase inhibitor cocktail (Pierce Halt, Thermo Scientific, Inc., Rockford, Ill.). After centrifugation, supernatants were incubated with ExoQuick exosome precipitation solution (EXOQ; System Biosciences, Inc., Mountain view, CA), and resultant suspensions centrifuged at 1,500×g for 30 min at 4° C. Each pellet was re-suspended in 300 μl of distilled water with inhibitor cocktails for immunochemical enrichment of exosomes from neural sources.

Total exosome suspensions were incubated with 2 μg of mouse anti-human CD171 (L1CAM, neural adhesion protein) biotinylated antibody (clone 5G3, eBioscience, San Diego, Calif.) in 50 μL of 3% BSA for 60 min at 20° C. followed by addition of 10 μl of Streptavidin-Plus UltraLink resin (Pierce-Thermo Scientific, Inc.) in 40 μL of 3% BSA and further incubation for 60 min. After centrifugation at 400×g for 5 min at 4° C., pellets were resuspended in 100 μl of 0.05 M glycine-HCl (pH 3.0), incubated at 4° C. for 10 min, and re-centrifuged at 4,000×g for 10 min at 4° C. Each supernate was transferred to a new Eppendorf tube containing 10 μL of 1 M Tris-HCl (pH 8.0) and 40 μL of 3% BSA, mixed and received 400 μL of M-PER mammalian protein extraction reagent (Thermo Scientific, Inc.) containing protease and phosphatase inhibitors, mixed and stored at −80° C. REST levels were quantified by human-specific ELISA (Cusabio, American Research Products, Inc., Waltham, Mass.) according to suppliers' directions. The tetraspanning exosome marker human CD81 (Cusabio-American Research Products, Inc.) was quantified, with verification of the CD81 antigen standard curve, using purified human recombinant CD81 antigen (Origene Technologies, Inc., Rockville, Md.), according to suppliers' directions.

Figure 8:
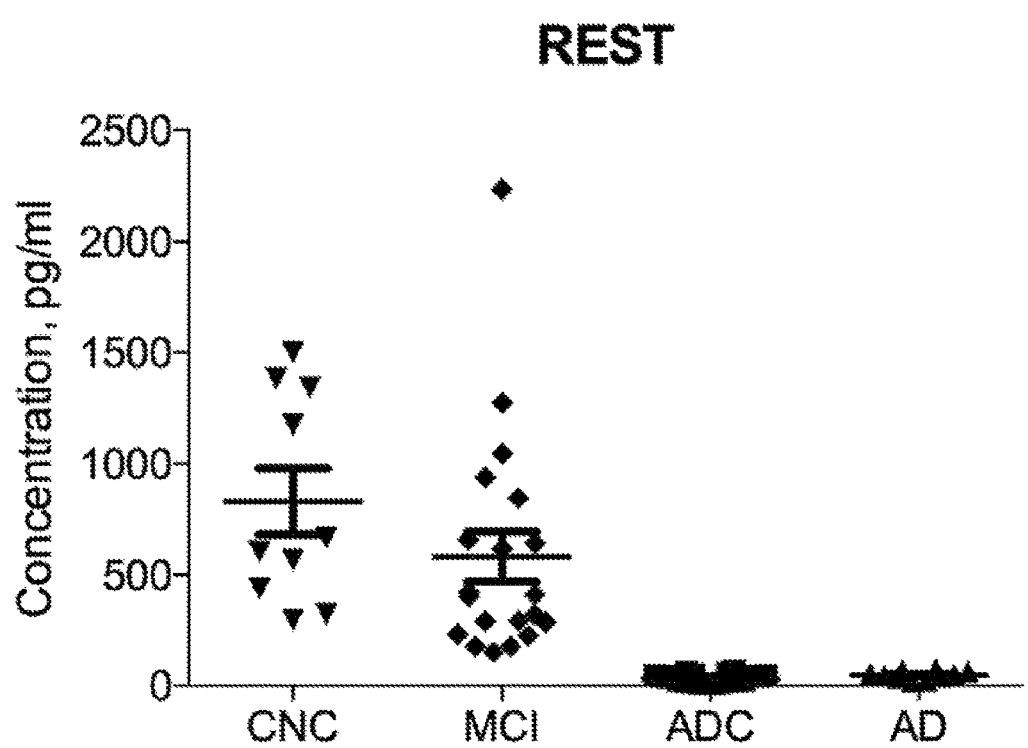
FIG. 8 sets forth data showing levels of REST in neural-derived plasma exosomes in cognitively normal controls (CNC), patients with Alzheimer's disease (AD), patients with mild cognitive impairment (MCI), and in patients that transitioned from MCI to AD (ADC).

As shown in FIG. 8, CD81-normalized NDE concentrations of REST were significantly lower in ADC patients (32.97±4.161 pg/ml) and in AD patients (48.17±5.661 pg/ml) compared to in MCI patients (582.0±112.5 pg/ml) and CNC subjects (829.9±148.4 pg/ml) (P<0.0001 for all differences). No significant difference between CD81-normalized NDE concentrations of REST in MCI patients as contrasted with CNC subjects was observed (see FIG. 8).

Receiver operating characteristic curve (ROC) analysis was conducted in order to determine if the diagnostic sensitivity of REST increased its predictive ability in distinguishing two patient populations. The sensitivity for distinguishing CNC from AD patients was 100% for REST. The sensitivity for distinguishing CNC from MCI patients was 71.5±0.09499 for REST. The sensitivity for distinguishing MCI from AD patients was 100% for REST.

These results showed that neuron-derived plasma exosomal levels of REST are lower in subjects with Alzheimer's disease (AD) and are useful for predicting the conversion of MCI to AD dementia in human subjects. These results also showed that REST was highly predictive for distinguishing AD patients from subjects with MCI. Additionally, these results showed that the assays and methods of the present invention may be useful for early detection and determining the progression of Alzheimer's disease. These results further indicated that methods and compositions of the present invention are useful for diagnosing Alzheimer's disease and other neurodegenerative disorders.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of analyzing a sample from a subject comprising the steps of: (i) obtaining a biological sample comprising neuron-derived exosomes from the subject, (ii) capturing neuron-derived exosomes from the biological sample, comprising: contacting the biological sample with at least one antibody under conditions wherein a neuron-derived exosome present in said biological sample binds to said antibody to form an exosome-antibody complex, wherein the antibody specifically binds NCAM, CD171, CD81, CD9, CD63, or neuron-specific enolase, thereby capturing said neuron-derived exosomes from said sample and (iii) detecting the level of one or more biomarkers from the neuron-derived exosomes with an immunoassay, wherein at least one of the one or more biomarkers is selected from the group consisting of low-density lipoprotein receptor-related protein 6, heat-shock factor-1 (HSF1), and repressor element 1-silencing transcription factor (REST), wherein the biological sample is plasma.

* * * * *